United States Patent [19]

Skinner

[11] 4,133,663
[45] Jan. 9, 1979

[54] REMOVING VINYL CHLORIDE FROM A VENT GAS STREAM

[75] Inventor: Ronald W. Skinner, Allentown, Pa.

[73] Assignee: Air Products and Chemicals, Inc., Allentown, Pa.

[21] Appl. No.: 671,122

[22] Filed: Mar. 29, 1976

[51] Int. Cl.² .............................................. F25J 3/00
[52] U.S. Cl. ........................................... 62/18; 62/23
[58] Field of Search ................. 260/654 S, 656 R; 62/18, 23, 40, 11; 55/68, 75, 76, 80, 89, 90; 526/77, 344

[56] References Cited

U.S. PATENT DOCUMENTS

| | | | |
|---|---|---|---|
| 2,503,939 | 4/1950 | De Baufre | 62/18 |
| 3,364,686 | 1/1968 | Becker | 62/18 |
| 3,534,562 | 10/1970 | Thijssen | 62/18 |
| 3,546,192 | 12/1970 | Borsini | 526/77 |
| 3,808,184 | 4/1974 | Sheth | 526/344 |

OTHER PUBLICATIONS

Condensed Chemical Dictionary — Hawley, 8th Ed., Van Nostrand Reinhold Co., N.Y., 1971, p. 927.
Cryogenic Engineering — Scott D. Van Nostrand Co. Inc., N.Y., 1959, pp. 271, 272, 277.

*Primary Examiner*—Hiram H. Bernstein
*Attorney, Agent, or Firm*—Russell L. Brewer; Barry Moyerman

[57] ABSTRACT

This invention relates to an improvement in a process for removing gaseous vinyl chloride monomer from a vent gas stream containing water, carbon dioxide, vinyl chloride, and other atmospheric gases. The process comprises cooling the vent gas stream to a temperature of from about −200° F to about −240° F for condensing the vinyl chloride, separating the condensed vinyl chloride from the noncondensed stream, and then recovering the refrigeration from the resulting stripped vent gas.

1 Claim, 1 Drawing Figure

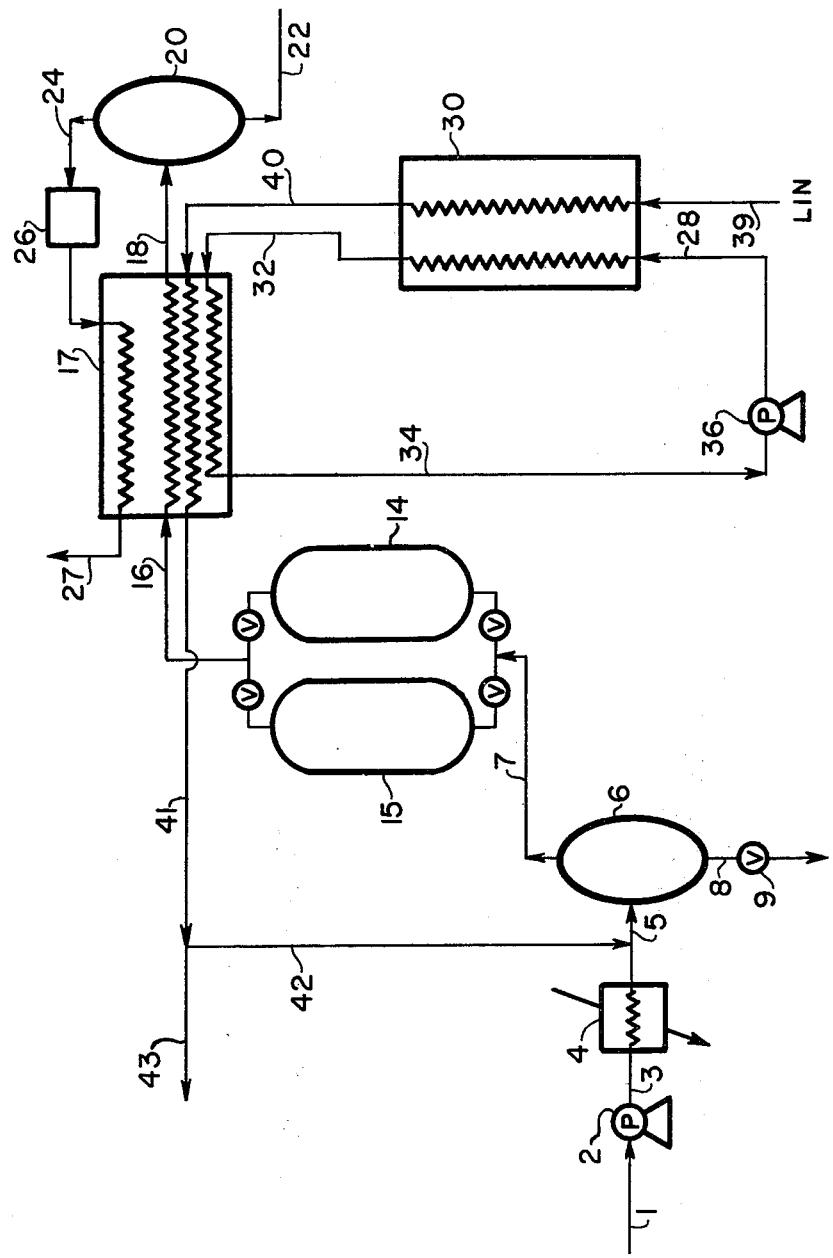

REMOVING VINYL CHLORIDE FROM A VENT GAS STREAM

BACKGROUND OF THE INVENTION

In the polymerization of vinyl chloride, whether it is by a batch or continuous method, generally there is some unreacted vinyl chloride monomer. This unreacted monomer normally has been vented from the product or stripped from the product in a stripping operation and then discharged as a vent gas stream to the atmosphere. Although this process was clearly acceptable in the early days of polyvinyl chloride production, this method has now come under attack. Recently investigators have found that vinyl chloride, when inhaled, may be carcinogenic and in order to prevent the possibility of harm to people, environmental standards have been issued by the government. These standards now require that the concentration of vinyl chloride, as monomer, in a gas stream which is to be discharged to the atmosphere be less than about 20 parts per million, and preferably less than about 10 parts per million.

DESCRIPTION OF THE PRIOR ART

Several processes have been proposed to remove vinyl chloride from a vent gas stream in order to meet these regulations. One method for removing vinyl chloride monomer from a vent gas stream is shown in U.S. Pat. No. 3,796,023. In this patent, vinyl chloride is absorbed onto an activated carbon, typically impregnated with hydroquinone, and then steam stripped from the carbon. One of the problems with this technique has been the inability to reduce the vinyl chloride monomer concentration in large volumes of gas to less than about 20 parts per million and the inability to prevent the escapement of vinyl chloride monomer to the atmosphere in the steam regenerating cycle and on disposal of the carbon.

U.S. Pat. No. 2,875,586 discloses methods for purifying vinyl chloride prepared from acetylene and hydrogen chloride. First, the gas is washed with water for removing hydrogen chloride and then dried with caustic potash or caustic soda. The gas then is distilled at temperatures of from $-10°$ C to $-20°$ C to remove low boiling constituents from the vinyl chloride.

U.S. Pat. No. 3,796,641 discloses a method for separating vinyl chloride from a vinyl chloride feed containing low molecular weight hydrocarbons, e.g. butane and butene. The process is also applicable for removing vinyl chloride from inert gases and comprises dissolving the vinyl chloride in dichloroethane and then distilling the vinyl chloride from the dichloroethane. Some of the problems associated with this process are; one, it is extremely difficult to reduce the vinyl chloride monomer to less than about 20 parts per million and thereby meet the standards imposed by governmental bodies and; two, there is the possibility of atmospheric emission of dichloroethane solvent during the distillation cycle.

Another process for the removal of vinyl chloride monomer from an inert gas stream has been to oxidize the vinyl chloride monomer by burning. Of course the vinyl chloride monomer present is lost and cannot be recovered for subsequent use.

SUMMARY OF THE INVENTION

This invention relates to an improvement in a process for removing gaseous vinyl chloride monomer from a vent gas stream containing water, carbon dioxide, vinyl chloride and inert atmospheric gases. The process comprises the steps:

reducing the concentration of water in the vent gas stream to less than about 20 ppm and preferably less than 1 ppm;

reducing the carbon dioxide in the vent gas stream to less than about 20 ppm and preferably less than 1 ppm;

cooling the vent gas stream in a cooling zone to a temperature of from about $-200°$ F to $-240°$ F for condensing substantially all of the vinyl chloride from the cooled gas stream;

separating the condensed vinyl chloride from the cooled gas stream forming a stripped gas stream;

recycling the stripped gas stream to the cooling zone for recovering the refrigeration therefrom; and recovering the vinyl chloride.

Advantages of this process include:

the ability to remove vinyl chloride monomer in a gas stream containing water, carbon dioxide and other gases to an extremely low level, e.g. 20 parts per million and preferably less than 10 ppm in a highly efficient manner;

the ability to recover substantial quantities of vinyl chloride monomer which, in the past, have been lost;

the ability to avoid flammable conditions in the removal of vinyl chloride from the vent gas stream thereby enhancing plant safety; and the ability to recover vinyl chloride monomer from a vent gas stream using simple mechanical equipment and processing techniques which minimize the production problems.

THE DRAWING

The drawing is a process flow diagram of the preferred embodiment for removing vinyl chloride monomer from a vent gas stream.

DESCRIPTION OF THE PREFERRED EMBODIMENTS

Referring to the drawing, a vent gas stream typically containing from about 95–50% air, 0.05–2% water, 0.05–2% carbon dioxide and 5–50% vinyl chloride monomer obtained from a polymerization reactor at a temperature of from about 60–100° F and a pressure of 15 psig is charged through inlet 1 through blower 2 and compressed to a pressure of about 65 psig. Operating pressures of about 50 to about 100 psig are preferred although such pressures are not mandatory. The vent gas stream then is passed through line 3 to cooler 4. Cooler 4 utilizes an ethylene glycolwater mixture for cooling the gas stream to a temperature of about 20° F. Typically, the gas stream is cooled to a temperature of from about 15° F–40° F. Most of the water and some vinyl chloride in the gas stream on cooling in cooler 4 condenses. The vapor and liquid are removed by line 5 to phase separator 6. There the water is removed from the bottom of phase separator 6 through line 8 and valve 9. Typically, phase separator has a screen or other mist eliminator pad (not shown) to aid in removing entrained droplets in the vapor stream.

The vapor from phase separator 6 is removed through line 7 and is passed through one of regenerating beds 14 and 15. These beds contain a conventional molecular sieve and are effective for removing residual water and carbon dioxide to less than about 1 ppm. When one bed is spent, the feed vapor is directd through the other bed and the spent bed regenerated in conventional manner. The vent gas leaving beds 14 or 15 through line 16 is substantially free of water and carbon dioxide. If the water and carbon dioxide are not removed, e.g. to a level below about 20 ppm and preferably 1 ppm water and carbon dioxide, and below during these stages, there may be freezing and plugging of equipment downstream.

The water-carbon dioxide free gas is directed by line 16 to heat exchanger 17, which is a coil wound heat exchanger. In heat exchanger 17, the vent gas is cooled to a temperature of from $-200°$ F to $-240°$ F. Typically, the gas is cooled to about $-225°$ F. This cooling process results in condensing out substantially all of the vinyl chloride monomer in the vent gas stream, and at this pressure the concentration of vinyl chloride monomer in the gas stream is less than about 20 parts per million. Generally the temperature is adjusted so there are less than 10 parts vinyl chloride per million parts vent gas stream. The cooled gas stream is withdrawn from heat exchanger 17, through line 18 and the condensed vinyl chloride monomer is separated from the noncondensed gas, e.g. oxygen, nitrogen and other atmospheric gases in phase separator 20. The condensed vinyl chloride monomer is withdrawn from phase separator 20 through line 22 and then is discharged to a distillation column or to a production tank for subsequent use in the polymerization process. The vapor from phase separator 20 is withdrawn through line 24 and passed through absorber 26 which contains activated carbon for removal of any residual vinyl chloride which may be in the gas stream. After leaving carbon absorber 26 at $-200$ to $-240°$ F, the stripped vent gas is recycled through heat exchanger 17 for recovering the refrigeration therefrom and then vented to the atmosphere via line 27. The gas vented to the atmosphere generally has a vinyl chloride concentration of less than 1 ppm when the carbon absorber is employed, and about 10 ppm when it is not.

The refrigeration balance in heat exchanger 17 is partially supplied by circulating a conventional refrigerant such as a nitrogen, fluorinated hydrocarbon, e.g. a Freon or conventional multicomponent refrigerant in a closed loop. The refrigerant is introduced by line 28 to heat exchanger 30 and cooled against cryogenic or liquid nitrogen. The refrigerant is withdrawn from heat exchanger 30 through line 32 and then passed to heat exchanger 17. The temperature of the refrigerant leaving heat exchanger 30 generally is from about $-245°$ F, but can be varied as desired, and the temperature of the refrigerant leaving heat exchanger 17 is about $-35°$ F.

The nitrogen used for cooling the multicomponent refrigerant is introduced by line 39 to heat exchanger 30. It is withdrawn by line 40 and then passed to heat exchanger 17. There it is warmed against the vent gas stream to a temperature of about $-35°$ F and withdrawn through line 41. Often a fraction of the nitrogen gas from heat exchanger 17 is recycled by line 42 to join the vent gas stream as it leaves cooler 4. Not only does the nitrogen provide refrigeration but it prevents the formation of a flammable gas stream. Because some vinyl chloride is condensed in phase separator 6, it is possible to pass through the flammability zone, i.e. a condition where the vinyl chloride content is above 4% and the oxygen content is above 13%, and create a hazardous condition. To avoid this condition then, sufficient nitrogen is added to the vent stream to reduce the oxygen content below 13%.

Although the above description shows a preferred embodiment of the invention, it is not intended to be exhaustive and certainly other variations are contemplated. For example, the vent gas can be cooled by injecting a liquefied gas, e.g., nitrogen, directly into the vent gas stream rather than by cooling in a heat exchanger. Also, the water can be removed by employing a conventional desiccant, e.g. silica gel in an absorber rather than in a cooler as shown.

What is claimed is:

1. A process for forming an environmentally acceptable vent gas stream having a vinyl chloride concentration of 10 parts per million or less from a vinyl chloride polymerization process wherein said vent gas from said process contains water, carbon dioxide, vinyl chloride, oxygen, and inert gas which comprises the steps:
   (A) reducing the concentration of water in the vent gas stream to less than 1 part per million;
   (B) reducing the carbon dioxide content in the vent gas stream to less than 1 part per million;
   (C) cooling the vent gas stream to a temperature of $-215$ to $-235°$ F in indirect heat exchange using cryogenic nitrogen as the refrigerant thereby forming a vinyl chloride condensate in said vent gas stream;
   (D) combining a sufficient proportion of the thus warmed refrigerant nitrogen in Step C with the vent gas stream prior to cooling to reduce the oxygen concentration to a level below the flammability range;
   (E) separating the condensed vinyl chloride from the thus cooled gas stream in Step C;
   (F) separating the condensed vinyl chloride from the cooled gas stream thereby forming a stripped gas stream and a vinyl chloride condensate;
   (G) recycling the stripped gas stream to the cooling zone for recovering the refrigeration therefrom;
   (H) passing said stripped gas stream through an activated carbon bed to remove residual vinyl chloride; and
   (I) recovering condensed vinyl chloride from separation Step F.

* * * * *